United States Patent [19]

Miller

[11] Patent Number: 6,039,698

[45] Date of Patent: Mar. 21, 2000

[54] METHOD AND APPARATUS FOR REMOVING BARRIER-TYPE CLOSURES FROM BLOOD COLLECTION TUBES

[75] Inventor: Henry F. Miller, Clifton, N.J.

[73] Assignee: Becton Dickinson and Company, Franklin Lakes, N.J.

[21] Appl. No.: 09/165,588

[22] Filed: Sep. 30, 1998

[51] Int. Cl.[7] .................................................. A61B 10/00
[52] U.S. Cl. ............................................. 600/576; 215/200
[58] Field of Search ................................... 600/573, 576, 600/575, 579, 578; 215/200, 232

[56] References Cited

U.S. PATENT DOCUMENTS

| | | | |
|---|---|---|---|
| 5,084,034 | 1/1992 | Zanotti | 604/319 |
| 5,275,730 | 1/1994 | Jahn | 210/578 |
| 5,377,854 | 1/1995 | Cusack | 215/364 |
| 5,575,317 | 11/1996 | Behnke, III et al. | 141/372 |
| 5,673,737 | 10/1997 | Behnke, III et al. | 141/372 |
| 5,764,731 | 10/1999 | Kovelman | 604/110 |

*Primary Examiner*—Cary O'Connor
*Assistant Examiner*—Pamela Wingood
*Attorney, Agent, or Firm*—Hoffmann & Baron, LLP; Nanette S. Thomas, Esq.

[57] ABSTRACT

A covered medical specimen container comprises a collection tube having an open upper end defined by a perimetrical rim. A cover is positioned over the open end and removably attached to the rim. A removable cap is positioned over the cover at a location spaced from the rim. Removal of the cover is achieved by exerting a removal force on the cap which the cap transforms into a localized peeling force that progresses around the entire rim.

12 Claims, 4 Drawing Sheets

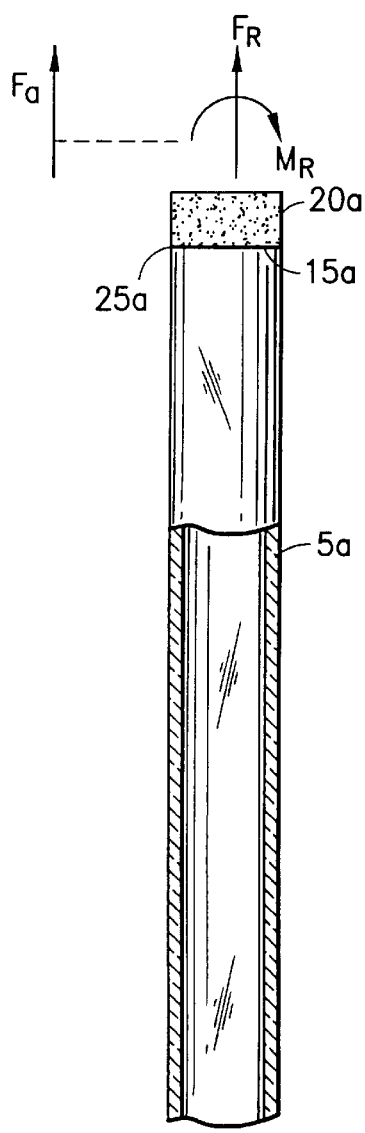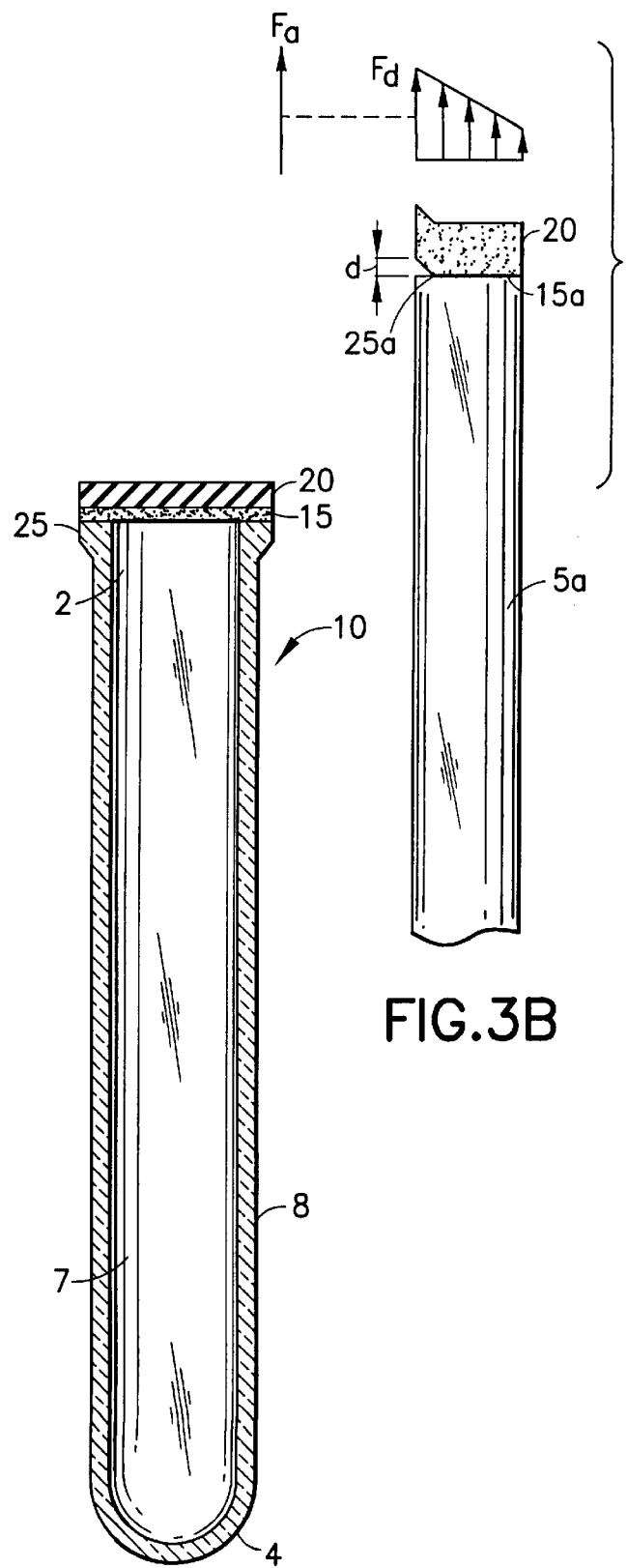
FIG.3A
FIG.3B
FIG.1

METHOD AND APPARATUS FOR REMOVING BARRIER-TYPE CLOSURES FROM BLOOD COLLECTION TUBES

BACKGROUND OF THE INVENTION

1. Field of the Invention

The present invention relates to a method for removing a cover from a medical specimen collection container. More specifically, the present invention relates to a method and apparatus for peeling the cover from a blood collection tube.

2. Description of Related Art

Blood samples and other medical specimens are routinely taken and collected in a specimen collection container. In blood collection applications, the collection container is typically a hollow blood collection tube with one end closed and the other end open. The open end is sealable by an elastomeric cover adhesively bonded to the rim around the open end of the tube. The tube thus defines an interior chamber for collecting and holding the blood specimen.

Blood is typically transferred into the interior chamber through a hollow blood collection needle which is placed in communication with the blood stream of the patient. The blood collection needle punctures the elastomeric cover to thus put the interior chamber in communication with the blood stream of the patient. When the phlebotomist has collected enough blood sample in the tube, the needle is withdrawn, and the elastomeric cover compresses on the hole made by the needle therethrough to effect a reseal of the blood collection tube. Thereafter, the blood sample may be analyzed or otherwise handled by a technician. The blood may be removed from the tube either through a hollow needle puncturing the cover or by removing the cover from the tube to access the contents. Furthermore, even where the contents are removed by a needle through the cover, a residual amount of blood sample will remain in the tube until the cover is removed therefrom.

The adhesive bond holds the elastomeric cover to the tube very securely. The integrity of the seal about the entire rim of the tube is maintained even when subjected to high torsional and tensile loads. Removing the cover can therefore be difficult. If the removal forces acting on the cover cause an abrupt failure of the adhesive bond, the tube may jar in the technician's hand and spill its contents on the technician.

It is therefore desirable to provide a method for removing the covers from the blood collection tubes in a smooth and controlled manner to prevent an abrupt separation of cover from tube that could spill or otherwise cause the contents to come into contact with the phlebotomist or technician.

SUMMARY OF THE INVENTION

The present invention is a method for manually removing a cover from a blood collection tube in a smooth and safe manner. Most prefereably, the present invention is a method for transferring an applied removal force to create localized failure of the adhesive bond between the cover and the blood collection tube and that continuously propagates the localized failure along the length of the seal.

Preferably, the present invention comprises a cover which is removable from a blood collection tube in a manner that reduces risk of blood contact with the technician.

Most preferably, the present invention is a method for removing a cover secured to the rim of the open end of a blood collection tube. The method involves applying unbalanced removal forces to the cover to cause a localized separation between the cover and the tube which will then propagate along the entire length of the seal. This technique effects a peeling action that separates the cover from the tube in a continuous and smooth motion that reduces the risk of the technician coming into contact with the contents of the tube. The removal force is applied to a cap positioned over the cover and which is attached to the cover at a location spaced from the rim of the tube. The removal force is transferred from the cap to the cover at the attachment location.

DESCRIPTION OF THE DRAWINGS

FIG. 1 shows, in section, a blood collection tube with a cover bonded to its open end.

FIG. 3A shows schematically the principle of inducing a peel-directed force on the cover of blood collection tube.

FIG. 3B is a schematic representation, similar to FIG. 3A, showing the peeling forces acting on the adhesive interface between the cover and the blood collection tube.

DETAILED DESCRIPTION

Figure 2:
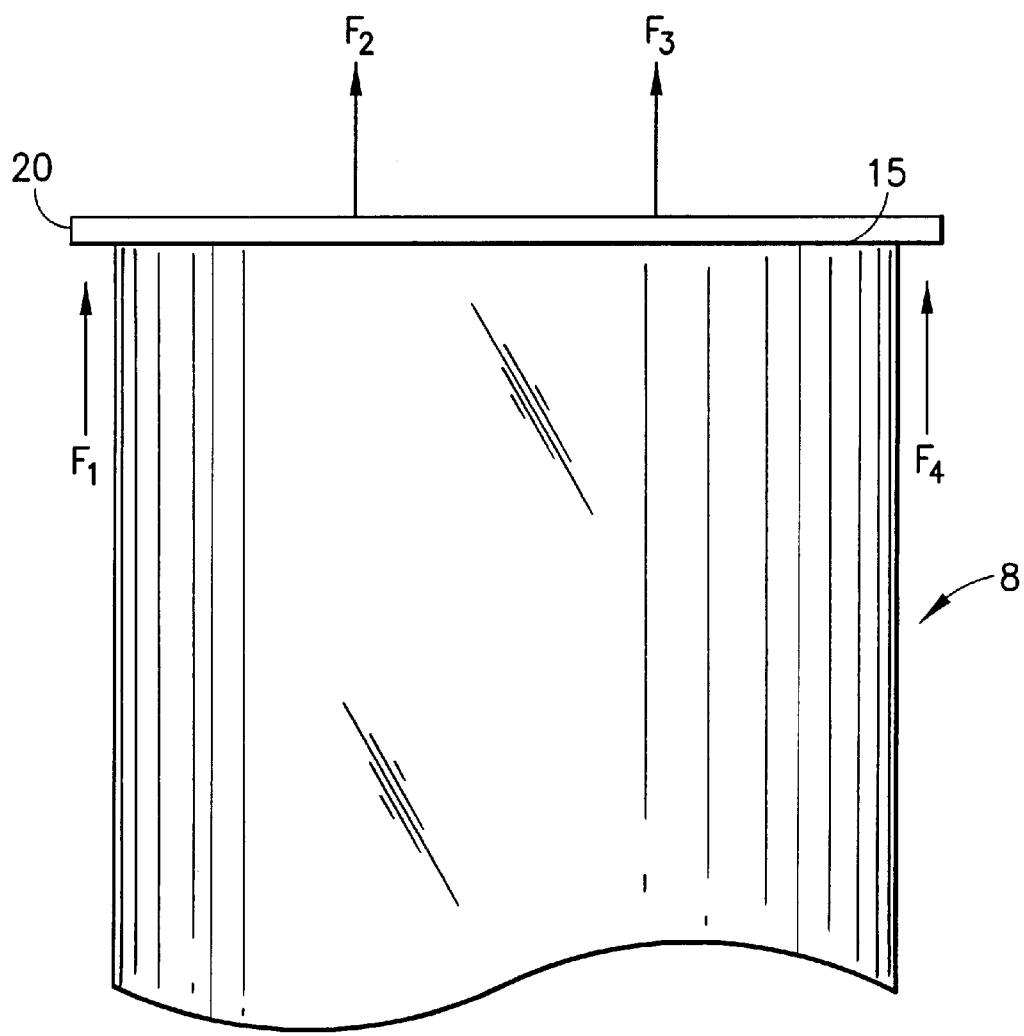
FIG. 2 is a schematic representation of the peel-directed forces that may be applied to the cover of a blood collection tube.

The present invention may be described as a technique for removing a cover from a blood medical specimen collection container. More specifically, the present invention, in a preferred embodiment, imparts a peeling action to remove the cover from a blood collection tube.

Referring to FIG. 1, in a typical blood collection procedure, a blood collection tube 10 is used to collect a blood sample from the circulatory system of a patient. The blood collection tube 10 is typically a hollow cylindrical tube 8 having one end closed by a semi-spherical closure 4 and an opposed open end 2, defined by rim surface 25. Blood collection tube 10 includes an interior chamber 7 in which to collect blood samples. Open end 2 is covered with an impermeable elastomeric cover 20 which is bonded to rim 25 by an adhesive interface 15. The bond between the cover 20 and the tube 8 must be sufficiently secure so as to provide for both the safety of the technicians taking or handling the blood sample, and for maintaining the blood sample within the collection tube 10.

However, for various purposes such as testing, analyzing, and the like, it is necessary to remove the elastomeric cover 20 from tube 8. In such situations, the adhesive forces between the cover 20 and tube 8 must be overcome. The seal between the cover and the tube is sufficiently strong so as to resist a typical load that is simultaneously applied across the entire adhesive interface 15 such as a purely tensile or torsional load. Overcoming the seal requires that the removal forces be localized to act on only a small portion of the adhesive interface 15 at any given time. The present invention provides a technique for localizing the removal forces on cover 20 to thereby effectively peel cover 20 from the rim of tube 8.

As shown in FIG. 2, the present invention provides a technique to transfer a force onto a blood collection tube cover at some point radially distant from the adhesive interface 15 which results in a peeling force being applied at some localized area of the interface 15. Peel-directed forces, designated $F_1$, $F_2$, $F_3$, and $F_4$ may be applied to the cover at locations which are spaced from the wall of tube 8. The peel-directed forces can act at any location on cover 20 away from the rim surface defining interface 15. The present invention is directed to applying the force at any convenient location away from the tube wall and interface 15.

Peel-directed forces $F_1$, $F_2$, $F_3$, and $F_4$ produce a bending moment on interface 15 which is resisted by a relatively small contact area. The resulting stress is very high and the interface joint fails locally. Continued application of the load results in localized failure which progresses around the tube and the cover is thereby completely separated from the tube using relatively light finger loading.

FIG. 3A shows how the peel-directed forces effectively peel a cover 20 from the rim 25 of a blood collection tube 8. Tube wall section 5$a$ is shown with cover section 20$a$ and a peel-directed force $F_a$ applied some distance from interface 15$a$. Force $F_a$ produces a resultant force $F_R$ and a bending moment $M_R$ at interface 15$a$. For the purposes of this illustration it is not necessary to designate whether tube surface 6 forms the interior surface or the exterior surface of tube 8 since the peeling principle is the same and the forces shown are relative to the interface. Resultant force $F_R$ and bending moment $M_R$ produce a distributed load $F_d$ across a radial extent of rim 25$a$ as shown in FIG. 3B. Load $F_d$ is further characterized as including a localized maximum force applied at that edge of the rim 25$a$ closest to applied removal force $F_a$. The localized maximum force causes failure of the bond at the edge of rim 25$a$ where it is applied, represented by separation d in FIG. 3B. The resulting peeling force and moment will then progress across the rest of interface 15 as cover 20 is peeled from tube 8.

Referring again to FIG. 2, peel-directed forces $F_1$, $F_2$, $F_3$, and $F_4$ may be directly applied to cover 20 or may be indirectly applied by a cap bonded to the exterior major surface of cover 20 at a location radially closer to the center of cover 20 than the rim tube 8 so as to produce peel-directed forces such as $F_2$ and $F_3$. Alternatively, the cover may be attached to the cap at a location radially exterior the outer diameter of rim 25 and thus produce peel-directed forces such as $F_1$ and $F_4$. Further, a cap could be attached to cover 20 at positions both radially interior and radially exterior to rim 25. With either type of a cap, the removal force applied to the cap will be transferred to cover 20, resulting in both a tensile force and a bending moment being applied to cover 20 at some localized area of interface 15.

Figure 4:
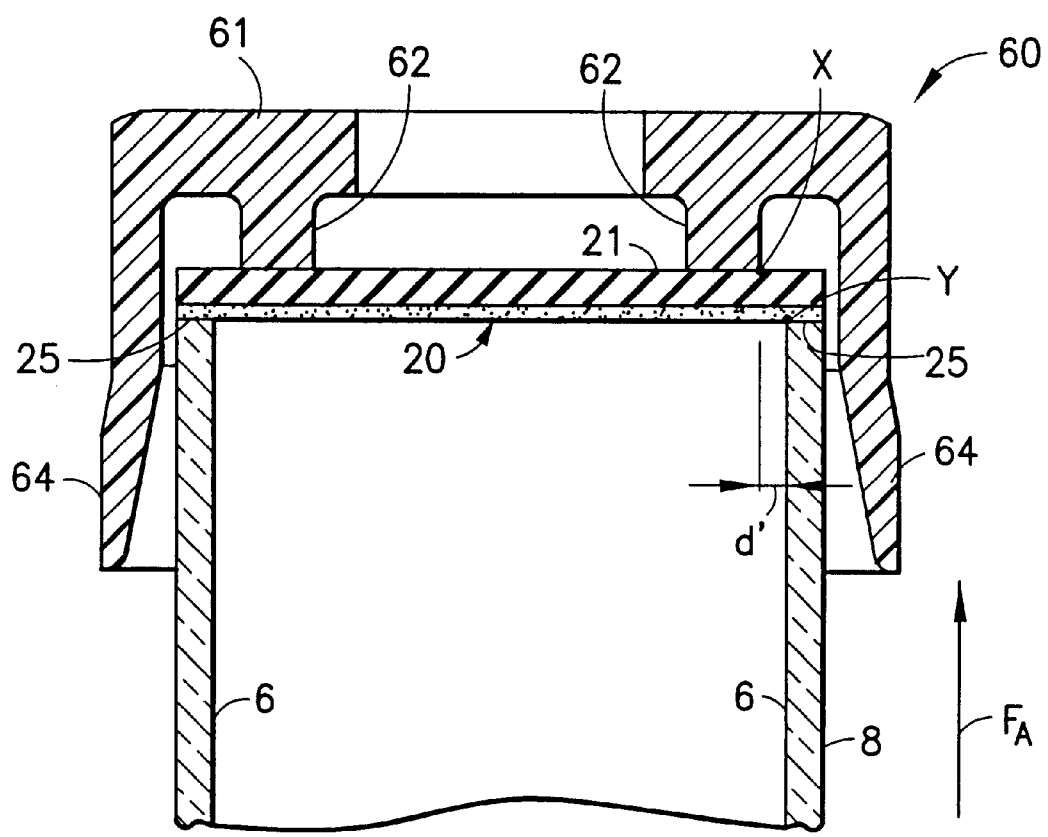
FIG. 4 shows a preferred embodiment of the present invention as applied to a cover bonded to a rim of a blood collection tube.

FIG. 4 shows one embodiment of a cap 60 that produces the peel-directed forces $F_2$ and $F_3$. Cap 60 includes a generally planar annular surface 61 and a depending annular component 62 which bonds to major surface 21 of cover 20 at an attachment loci which is coplanar and coaxial thereto. The attachment loci is radially displaced by a distance d' from the interior edge of rim 25. A removal force $F_A$ applied, for example, by pushing up on a single portion of flange 64 of cap 60, is transferred to cover 20 by the annular component 62 effectively producing peel-directed forces similar to $F_2$ and $F_3$ in FIG. 2. Of course with cap 60, the removal force is actually distributed about the length of annular component 62 and the removal force would also produce a moment about annular component 62. However, the forces and bending moment acting about annular component 62 may be represented by forces $F_2$ and $F_3$, with $F_3$ having greater magnitude than $F_2$. Cap 60 will therefore begin to peel cover 20, first at point Y on the innermost edge of rim 25 and then across rim 25 towards the portion of flange 64 where $F_A$ is applied, then progressively around rim 25 away from the portion of flange 64 where $F_A$ is applied in a manner described hereinabove.

Figure 5:
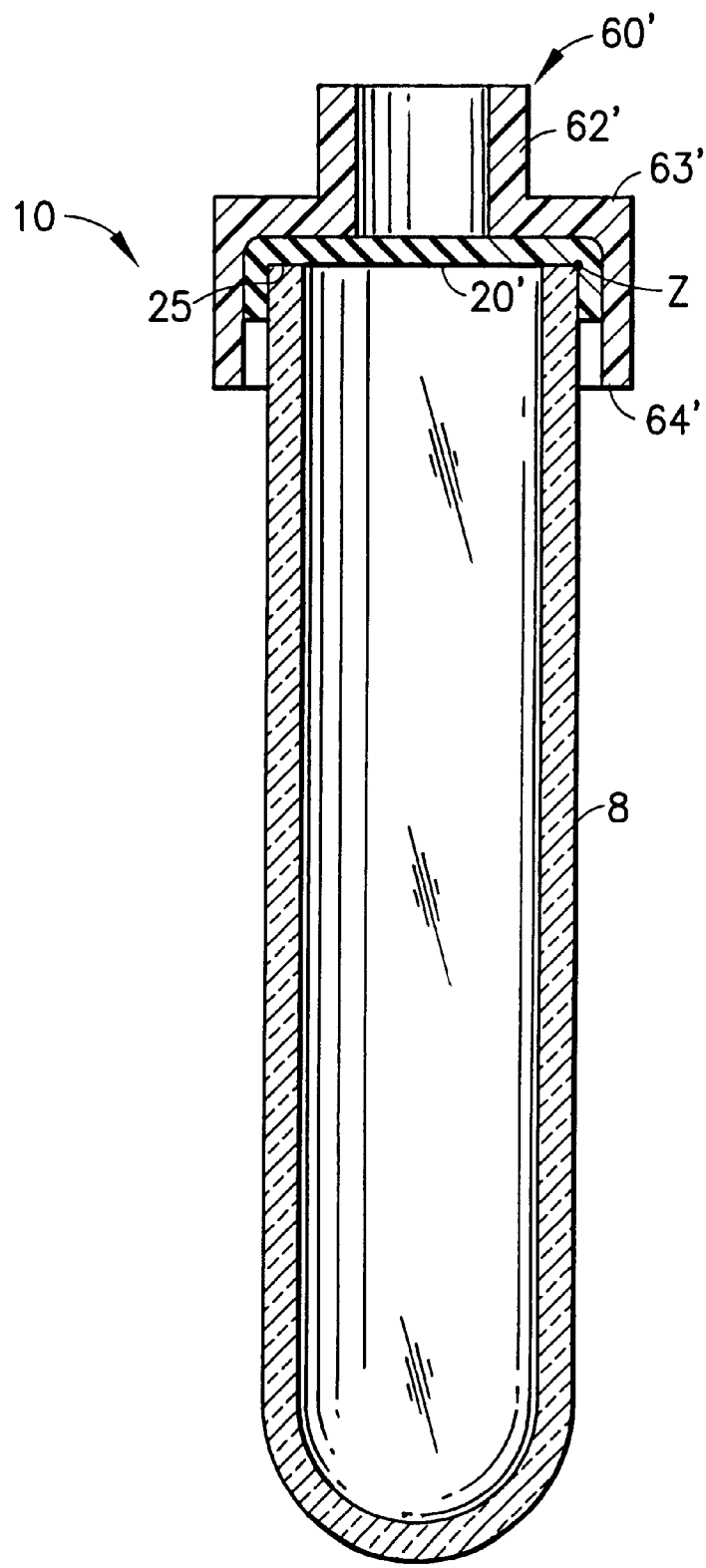
FIG. 5 shows an alternative embodiment of the present invention as applied to a cover bonded to the rim of a blood collection tube includes an over-extending rim which is bent down around the end of the tube.

Another embodiment of the present invention is shown in FIG. 5. A cap 60' may be used with a cover 20' having an outer diameter greater than rim 25 so as to provide an over-extended portion 24' which overhangs rim 25. Cap 60' includes an upwardly extending inner annular ring 62', and a downwardly extending outer annular ring 64'. An annular lip 63' connects the two annular rings. Cap 60', when forced onto cover 20', bends the over-extended portion 24' of the cover down around tube 8 as shown. Cover 20' is only attached to tube 8 at rim 25. However cap 60' is attached to cover 20', either by an adhesive bonding means or by friction. The bond between cap 60' and cover 20' is stronger than the bond between cover 20' and tube 8. Applying a removal force $F_A$ to a portion of outer annular ring 64' produces a peeling force similar to $F_4$ of FIG. 2. With this arrangement, cover 20' will begin to first peel from a point Z on the outermost diameter of rim 25 before progressively peeling in a direction diametrically across rim 25.

Various other modifications to the foregoing disclosed embodiments will now be evident to those skilled in the art. Thus, the particularly described preferred embodiments are intended to be illustrative and not limited thereto. The true scope of the present invention is set forth in the following claims.

What is claimed is:

1. In a blood collection tube having an open upper end defined by a perimetrical rim of said tube and a cover having a top surface and a bottom surface and positioned over the open end of said tube, said bottom surface being secured to said rim, a method of lifting said cover from said rim comprising the steps of:

positioning a cap over said cover, said cap being attached to said cover at a location spaced from said rim; and exerting a force on said cap, in a removal direction, said force being transferred to said cover at said attached location spaced from said rim.

2. The method of claim 1, wherein said force is a pulling force applied to said cap.

3. The method of claim 2, wherein said cap is attached to said cover at a location interiorly of said perimetrical rim.

4. The method of claim 2, wherein said cap is attached to said cover at a location exteriorly of said perimetrical rim.

5. The method of claim 1, wherein said cap is attached to said cover on said bottom surface of said cover.

6. A covered medical specimen container comprising:

a collection tube having an open upper end defined by a perimetrical rim;

a cover positioned over said tube open end and being removably attached to said rim;

a removable cap positioned over said cover, said removable cap being attached to said cover at a location spaced from said rim;

wherein removal of said cap exerts a removal force on said cover at a location of said attachment of said cap to said cover.

7. The container of claim 6, wherein said attachment of said cap to said cover is by a first adhesive bond and wherein said attachment of said cover to said rim is by a second adhesive bond, wherein said first adhesive bond is stronger than said second adhesive bond.

8. The container of claim 6, wherein said removal of said cap exerts a pulling force on said cover at said location spaced from said rim.

9. The container of claim 7, wherein said cap is attached to said cover at a location interior of said perimetrical rim.

10. The container of claim 6, wherein said cover includes a lower surface attached to said rim and an opposed upper surface.

11. The container of claim 10, wherein said cap is attached to said upper surface of said cover and removal of said cap exerts a pulling force on said cover.

12. The container of claim 10, wherein said cap is attached to said lower surface of said cover and exerts a pushing force on said cover.

* * * * *